(12) United States Patent
Jo et al.

(10) Patent No.: US 9,731,144 B2
(45) Date of Patent: Aug. 15, 2017

(54) LIGHT EMITTING ELEMENT DISPLAY DEVICE WITH LIGHT THERAPY DEVICE AND METHOD FOR DRIVING THE SAME

(71) Applicant: Samsung Display Co., Ltd., Yongin, Gyeonggi-do (KR)

(72) Inventors: Min Gyeong Jo, Yongin (KR); Jong In Baek, Yongin (KR); Byeong Hee Won, Yongin (KR); Won Sang Park, Yongin (KR)

(73) Assignee: Samsung Display Co., Ltd., Gyeonggi-do (KR)

( * ) Notice: Subject to any disclaimer, the term of this patent is extended or adjusted under 35 U.S.C. 154(b) by 121 days.

(21) Appl. No.: 14/748,553

(22) Filed: Jun. 24, 2015

(65) Prior Publication Data
US 2016/0016003 A1  Jan. 21, 2016

(30) Foreign Application Priority Data
Jul. 17, 2014 (KR) .................. 10-2014-0090549

(51) Int. Cl.
| | | |
|---|---|---|
| *G02F 1/1335* | (2006.01) | |
| *A61N 5/06* | (2006.01) | |
| *G02F 1/137* | (2006.01) | |
| *A61N 5/073* | (2006.01) | |
| *G02F 1/01* | (2006.01) | |

(52) U.S. Cl.
CPC .... *A61N 5/0616* (2013.01); *A61N 2005/0627* (2013.01); *A61N 2005/0653* (2013.01); *A61N 2005/073* (2013.01); *G02F 1/0136* (2013.01); *G02F 1/13725* (2013.01); *G02F 2203/62* (2013.01)

(58) Field of Classification Search
CPC .......... A61N 5/0616; A61N 2005/0627; G02F 1/0136
USPC .......................................................... 349/96
See application file for complete search history.

(56) References Cited

U.S. PATENT DOCUMENTS

| | | | |
|---|---|---|---|
| 8,759,864 B2 | 6/2014 | Kim et al. | |
| 2003/0098856 A1* | 5/2003 | Li | G02F 1/133502 345/173 |
| 2012/0045738 A1 | 2/2012 | Ho et al. | |

FOREIGN PATENT DOCUMENTS

| | | |
|---|---|---|
| KR | 10-2003-0036072 | 5/2003 |
| KR | 10-2007-0045382 | 5/2007 |
| KR | 10-2009-0122138 | 11/2009 |

(Continued)

OTHER PUBLICATIONS

Barolet, Daniel, "Light-Emitting Diodes (LEDs) in Dermatology", Seminars in Cutaneous Medicine and Surgery, pp. 227-238, Elsevier, Inc., 2008.

(Continued)

*Primary Examiner* — Lucy Chien
(74) *Attorney, Agent, or Firm* — Knobbe Martens Olson & Bear LLP (57) ABSTRACT

A light emitting element display device can be used for light therapy. The device includes: a display panel including a plurality of light emitting elements; a retarder plate configured to convert light emitted from the plurality of light emitting elements into circularly polarized light; and a selective polarizer configured to selectively convert light supplied from the retarder plate into linearly polarized light or allow penetration of the light.

16 Claims, 10 Drawing Sheets

(56) References Cited

FOREIGN PATENT DOCUMENTS

| KR | 10-2011-0015976 | 2/2011 |
|----|-----------------|--------|
| KR | 10-2012-0018050 | 2/2012 |

OTHER PUBLICATIONS

Uchida, Tatsuo, et al., "Bright Dichroic Guest-Host LCDs Without a Polarizer", Tohoku University, pp. 41-46, Proceeding of the SID, vol. 22/1, 1981.

* cited by examiner

LIGHT EMITTING ELEMENT DISPLAY DEVICE WITH LIGHT THERAPY DEVICE AND METHOD FOR DRIVING THE SAME

CROSS-REFERENCE TO RELATED APPLICATION

This application claims priority to and the benefit of Korean Patent Application No. 10-2014-0090549, filed on Jul. 17, 2014, with the Korean Intellectual Property Office, the disclosure of which is incorporated herein in its entirety by reference.

BACKGROUND

Field

The present disclosure relates to a light emitting element display device having a light therapy function, and to a method of driving the light emitting element display device.

Description of the Related Technology

In recent years, a treatment for skin problems using light emitted from a light emitting diode (LED) has been performed. When human skin is irradiated with light of an LED, the light infiltrates into the skin and becomes absorbed. The absorbed light is converted into thermal energy and the thermal energy may induce thermotherapy effects. More particularly, studies have reported that infrared light generates and activates nitric oxide in blood vessel endothelium, and the self-healing power is thus enhanced so that skin tone and texture are improved, and oxygen is increased in blood to remove toxins.

Such a treatment method using the light of the LED is simple and causes fewer side effects compared to conventional treatment methods, thereby extending the range of its application. However, there have been temporal and spatial limitations because such a treatment device has a large size and is priced high, and patients need to visit a clinic or a special location that has the treatment apparatus.

It is to be understood that this background of the technology section is intended to provide useful background for understanding the technology and as such disclosed herein, the technology background section may include ideas, concepts or recognitions that were not part of what was known or appreciated by those skilled in the pertinent art prior to a corresponding effective filing date of subject matter disclosed herein.

SUMMARY OF CERTAIN INVENTIVE ASPECTS

The present disclosure is directed to a light emitting element display device capable of being utilized as a light therapy device beyond its conventional function of displaying images and to a method of driving the light emitting element display device.

A light emitting element display device having a light therapy function may include: a display panel including a plurality of light emitting elements; a retarder plate configured to convert light emitted from the plurality of light emitting elements into circularly polarized light; and a selective polarizer configured to selectively convert light supplied from the retarder plate into linearly polarized light or allow penetration of the light.

The light emitting element display device may further include a polarization controller configured to control the selective polarizer based on selection of a display mode or a therapy mode.

The light emitting element display device may further include: a counter configured to count time from the time when the selective polarizer starts light penetration; and a polarization controller configured to compare the counted time supplied from the counter with a predetermined reference value and to control an operation of the selective polarizer based on a result of the comparison.

The selective polarizer may stop the light penetration by control of the polarization controller, when the counted time is the same as or larger than the predetermined reference value.

The selective polarizer may further carry out a polarization process by control of the polarization controller, when the light penetration is stopped.

The polarization controller may generate an alert, when the light penetration is stopped.

The selective polarizer may include: a lower substrate; an upper substrate disposed to face the lower substrate; a guest-host layer disposed between the lower substrate and the upper substrate; a lower electrode and an upper electrode respectively formed on facing surfaces of the lower substrate and the upper substrate; a lower alignment layer disposed on the lower electrode; and an upper alignment layer disposed on the upper electrode.

The guest-host layer may include liquid crystal molecules and dichroic dyes

An initial alignment direction of the liquid crystal molecules and the dichroic dyes may be one of a vertical direction and a horizontal direction.

A major axis of the liquid crystal molecules aligned in the horizontal direction and an optical axis of the retarder plate may form an angle of about 45 degrees.

The display panel may include a substrate, and a driving circuit disposed on the substrate and configured to drive the plurality of light emitting elements and the plurality of light emitting elements may be disposed on the driving circuit.

According to an embodiment, a method of driving the light emitting element display device having a light therapy function may include: arranging a display panel comprising a plurality of light emitting elements, a retarder plate configured to convert light emitted from the plurality of light emitting elements into circularly polarized light, and a selective polarizer configured to selectively convert light supplied from the retarder plate into linearly polarized light or to allow penetration of the light; and controlling the selective polarizer based on selection of a display mode or a light therapy mode.

The method may further include: counting time from the time when the selective polarizer starts a light penetration process; and comparing the counted time with a predetermined reference value and controlling an operation of the selective polarizer based on a result of the comparison.

The method may further include controlling the selective polarizer to stop the light penetration, when the counted time is the same as or larger than the predetermined reference value.

The method may further include controlling the selective polarizer to further carry out a polarization process, when the light penetration is stopped.

The method may further include generating an alert, when the light penetration is stopped.

According to embodiments, a light emitting element display device is capable of performing a light therapy function utilizing light emitting elements that are used for displaying images. More particularly, the light emitting element display device is capable of easily converting a display mode and a light therapy mode by adjusting an amount of light by using a selective polarizer.

Further, according to embodiments, the light emitting element display device is capable of maximizing a light therapy effect and also preventing side effects by automatically limiting an amount of light radiation in a light therapy mode.

The foregoing is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The above and other features and aspects of the present disclosure will be more clearly understood from the following detailed description taken in conjunction with the accompanying drawings, in which.

DETAILED DESCRIPTION OF CERTAIN INVENTIVE EMBODIMENTS

Hereinafter, embodiments of the present disclosure will be described in more detail with reference to the accompanying drawings.

Although the present invention can be modified in various manners and have several embodiments, specific embodiments are illustrated in the accompanying drawings and will be mainly described in the specification. However, the scope of the embodiments is not limited to the specific embodiments and should be construed as including all the changes, equivalents, and substitutions included in the spirit and scope of the present invention.

Throughout the specification, when an element is referred to as being "connected" to another element, the element can be "directly connected" to the other element, or "electrically connected" to the other element with one or more intervening elements interposed therebetween. It will be further understood that the terms "comprises," "comprising," "includes" and/or "including," when used in this specification, specify the presence of stated features, integers, steps, operations, elements, and/or components, but do not preclude the presence or addition of one or more other features, integers, steps, operations, elements, components, and/or groups thereof.

It will be understood that, although the terms "first," "second," "third," and the like may be used herein to describe various elements, these elements should not be limited by these terms. These terms are only used to distinguish one element from another element. Thus, "a first element" discussed below could be termed "a second element" or "a third element," and "a second element" and "a third element" can be termed likewise without departing from the teachings herein.

Some of the parts which are not associated with the description may not be provided in order to specifically describe embodiments, and like reference numerals generally refer to like elements throughout the specification.

Figure 1:
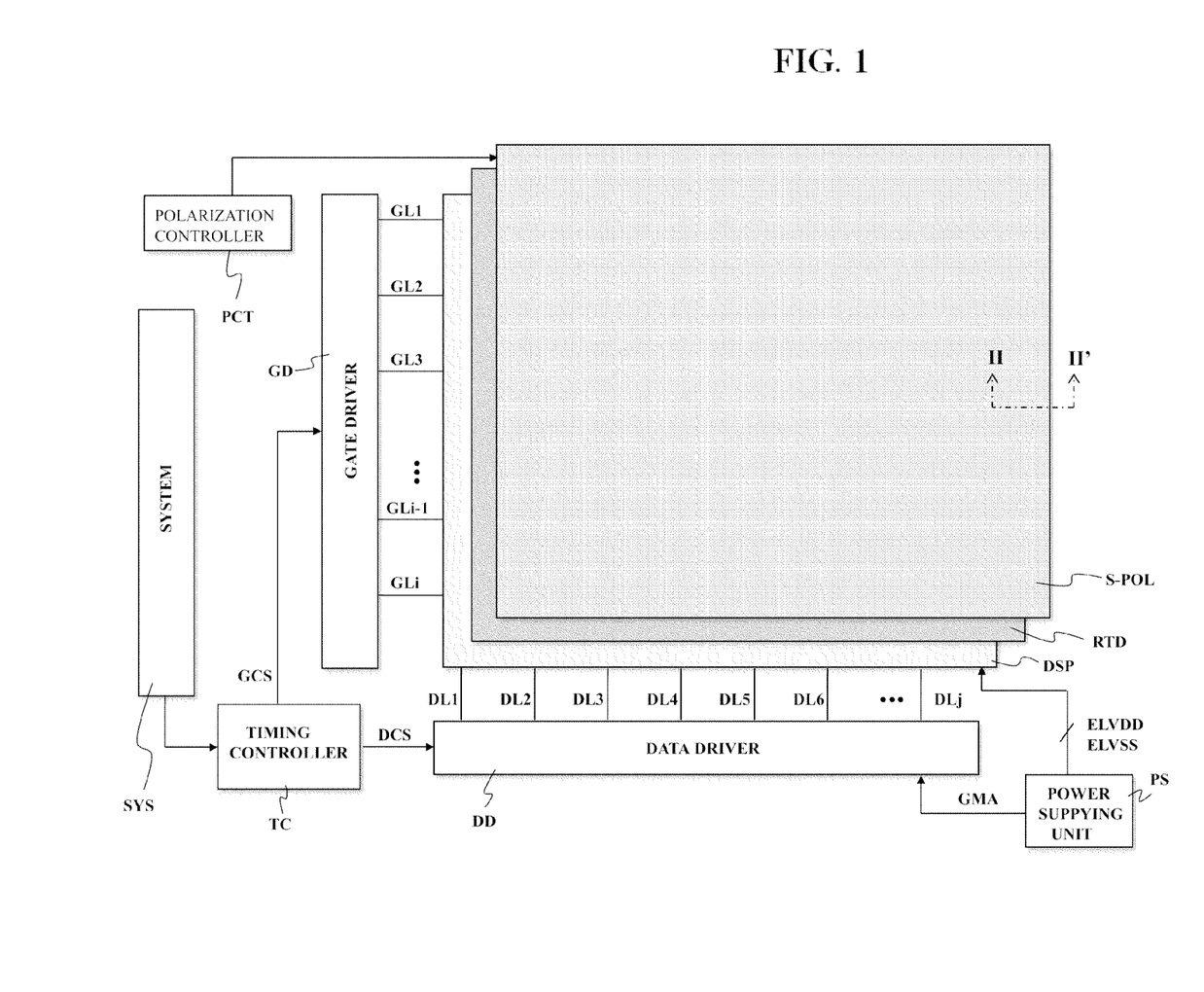
FIG. 1 is a conceptual view illustrating a light emitting element display device according to an embodiment.
Figure 2:
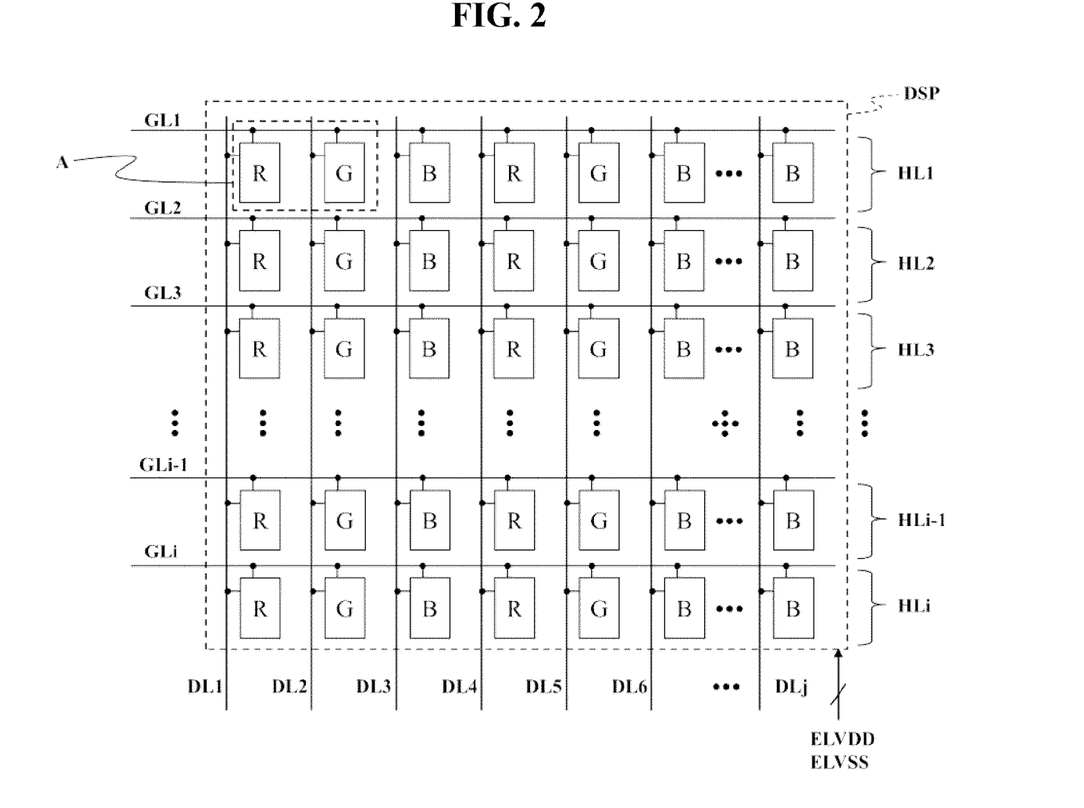
FIG. 2 is a detailed configuration view illustrating a display panel of FIG. 1.

FIG. 1 is a conceptual view illustrating a light emitting element display device according to an embodiment and FIG. 2 is a detailed configuration view illustrating a display panel of FIG. 1.

According to an embodiment, the light emitting element display device includes, as illustrated in FIG. 1, a display panel DSP, a retarder plate RTD, a selective polarizer S-POL, a timing controller TC, a data driver DD, a gate driver GD, a power supplying unit PS, and a polarization controller PCT.

The display panel DSP includes, as illustrated in FIG. 2, i×j pixels R, G, and B, i gate lines GL1 to GLi, and j data lines DL1 to DLj (i and j are natural numbers larger than 1). The respective ones of i×j pixels R, G, and B include a light emitting element (not illustrated).

First to $i^{th}$ gate signals are respectively applied to the first to the $i^{th}$ gate lines GL1 to GLi. Further, a data voltage is applied to the first to the $j^{th}$ data lines DL1 to DLj, respectively. Although not illustrated, the display panel DSP includes a first driving power line for supplying a first driving voltage ELVDD to the i*j pixels and a second driving power line for supplying a second driving voltage ELVSS to the i*j pixels.

The pixels R, G, and B are arranged in a display area of the display panel DSP in a matrix form. The pixels R, G, and B are categorized into red pixels R displaying a red color, green pixels G displaying a green color, and blue pixels B displaying a blue color. The red pixel R includes a red light emitting element emitting red light, the green pixel G includes a green light emitting element emitting green light, and the blue pixel B includes a blue light emitting element emitting blue light.

The red, green, and blue pixels R, G, and B adjacently disposed in a horizontal direction may become a unit pixel for displaying one unit image. J pixels arranged along an $n^{th}$ (n is a number selected from 1 to i) horizontal line (hereinafter, $n^{th}$ horizontal line pixels) are respectively connected to the first to the $j^{th}$ data lines (DL1 to DLj). Further, the $n^{th}$ horizontal line pixels are connected to the $n^{th}$ gate line together. Accordingly, the nth horizontal line pixels receive an $n^{th}$ gate signal together. That is, the j pixels aligned in the same horizontal line receive the same gate signal, while pixels aligned in different horizontal lines receive different gate signals. For example, both of the red pixel R and the green pixel G disposed on the first horizontal line HL1 receive a first gate signal, while the red pixel R and the green pixel G disposed on the second horizontal line HL2 receive a second gate signal that has a different timing compared to the first gate signal.

Hereinafter, a configuration of the display panel DSP will be described in more detail with reference to FIGS. 3 and 4.

Figure 3:
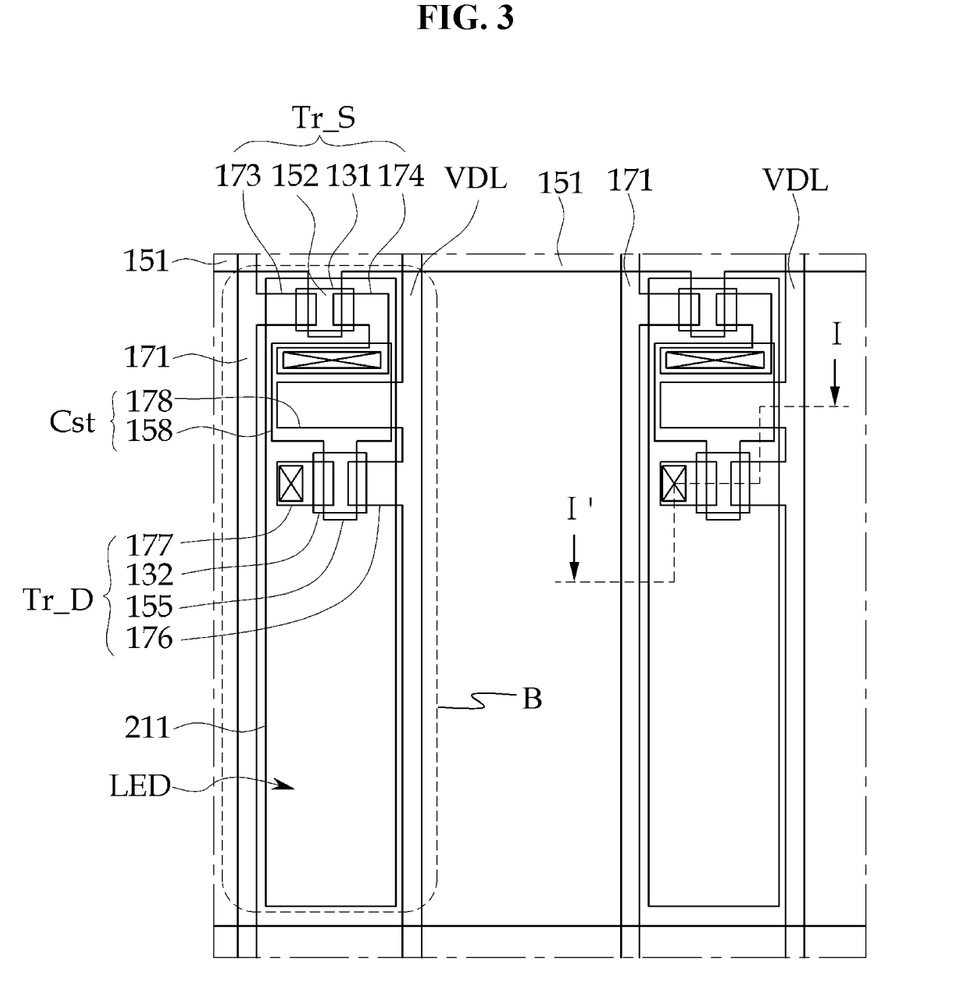
FIG. 3 is a partial plan view enlarging "A" part of FIG. 1.
Figure 4:
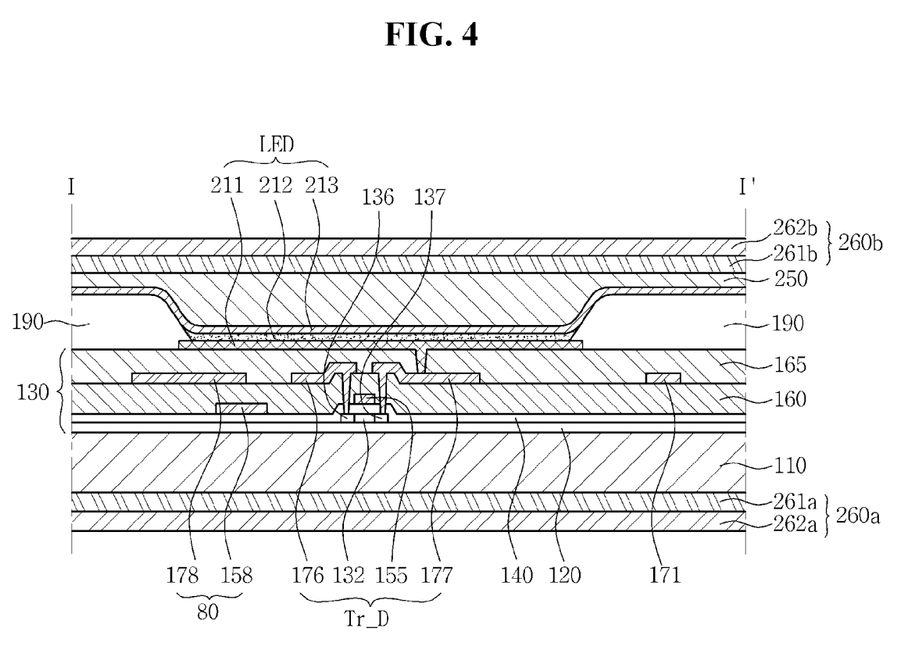
FIG. 4 is a cross-sectional view taken along a line I-I' of FIG. 3.

FIG. 3 is a partial plan view enlarging "A" part of FIG. 1 and FIG. 4 is a cross-sectional view taken along a line I-I' of FIG. 3.

Referring to FIGS. 3 and 4, the display panel DSP includes a substrate 110, a driving circuit 130 on the substrate 110, a light emitting element on the driving circuit 130, and a sealing member 250 on the light emitting element.

A display device 100 according to an embodiment may include a first coating layer 260a and this first coating layer 260a may be, in some embodiments, disposed on a rear surface of the substrate 110. Further, the display device 100 according to an embodiment may include a second coating layer 260b and this second coating layer 260b may be, in some embodiments, disposed between the sealing member 250 and a retarder plate RTD. The first coating layer 260a may include at least one of a water-resistant coating layer 261a and a heat-resistant coating layer 262a and the second coating layer 260b may include at least one of a water-resistant coating layer 261b and a heat-resistant coating layer 262b. The driving circuit 130 is disposed on the substrate 110. The driving circuit 130 includes a switching thin film transistor Tr_S, a driving thin film transistor Tr_D, and a light emitting element and is configured to drive the light emitting element. An organic light emitting element may be used as the light emitting element.

Although a detailed configuration of the driving circuit 130 and the light emitting element is disclosed in FIGS. 3 and 4, embodiments are not limited thereto. The driving circuit 130 and the light emitting element may be formed to have many different structures within the scope of the present invention with a modification those skilled in the pertinent art can easily conceive.

Referring to FIG. 3, one pixel is depicted as having two thin film transistors (TFTs) and one capacitor. However, embodiments are not limited thereto, and thus one pixel may include three or more thin film transistors and two or more capacitors and may have various structures including additional wires. Herein, a pixel refers to a smallest unit for displaying an image and may be one of the red pixel R, the green pixel G, and the blue pixel B.

Referring to FIGS. 3 and 4, the respective pixels include a switching thin film transistor Tr_S, a driving thin film transistor Tr_D, a capacitor Cst and a light emitting element. The driving circuit 130 refers to a structure including the switching thin film transistor Tr_S, the driving thin film transistor Tr_D, and the light emitting element.

The driving circuit 130 includes a gate line 151 disposed along one direction, a data line 171 insulated from and intersecting the gate line 151, and a first driving power line VDL. A pixel region is generally defined by the gate line 151, the data line 171, and the first driving power line VDL; however, the pixel region is not limited to the above description. That is, unlike the above-mentioned structure, the pixel region may be defined by a black matrix or a pixel defining layer 190.

The substrate 110 may be a transparent insulating substrate including glasses or transparent materials, such as, for example, plastics. In more detail, the substrate 110 may include at least one of kapton, polyethersulphone (PES), polycarbonate (PC), polyimide (PI), polyethyleneterephthalate (PET), polyethylenenaphthalate (PEN), polyacrylate (PAR), and fiber reinforced plastic (FRP).

A buffer layer 120 may be disposed on the substrate 110. The buffer layer 120 is configured to prevent infiltration of undesirable elements and planarize a surface and may include suitable materials for planarizing and/or preventing infiltration. For example, the buffer layer 120 may include one of the followings: a silicon nitride (SiNx) layer, a silicon oxide (SiO2) layer, and a silicon oxynitride (SiOxNy) layer.

However, the buffer layer 120 is not always necessary and may be omitted depending on kinds of the substrate 110 and process conditions thereof.

A switching semiconductor layer 131 and a driving semiconductor layer 132 are disposed on the buffer layer 120. The switching semiconductor layer 131 and the driving semiconductor layer 132 may include oxide semiconductors, such as, for example, a polycrystalline silicon film, an amorphous silicon film, indium-gallium-zinc oxide (IGZO), or indium zinc tin oxide (IZTO). For example, in a case where the driving semiconductor layer 132 illustrated in FIG. 4 includes the polycrystalline silicon film, the driving semiconductor layer 132 may include a channel region that is not doped with impurities and p+ doped source and drain regions that are formed on both sides of the channel region. In this case, p-type impurities, such as for example boron B, may be used as dopant ions, such as for example B2H6. Such impurities may vary depending on the kinds of thin film transistors. According to an embodiment, a PMOS (p-channel metal oxide semiconductor)-structured TFT using the p-type impurities is used as the driving TFT Tr_D, but embodiments are not limited thereto. Thus, an NMOS (n-channel metal oxide semiconductor)-structured or a CMOS (complementary metal oxide semiconductor)-structured TFTs may also be used as the driving TFT Tr_D.

A gate insulating layer 140 is disposed on the switching semiconductor layer 131 and the driving semiconductor layer 132. The gate insulating layer 140 may include at least one of tetraethylorthosilicate (TEOS), silicon nitride (SiNx), and silicon oxide (SiO2). For example, the gate insulating layer 140 may have a double-layer structure where a SiNx layer having a thickness of 40 nm and a TEOX layer having a thickness of 80 nm are sequentially laminated.

A gate wire including gate electrodes 152 and 155 is disposed on the gate insulating layer 140. The gate wire includes a gate line 151, a first capacitor plate 158, and other lines. Further, the gate electrodes 152 and 155 are disposed to overlap at least parts of the semiconductor layers 131 and 132, that is, more particularly, channel regions. The gate electrodes 152 and 155 are configured to prevent the channel regions from being doped with impurities when source and drain regions 136 and 137 of the semiconductor layers 131 and 132 are doped with impurities during the process of forming the semiconductor layers 131 and 132.

The gate electrodes 152 and 155 and the first capacitor plate 158 are disposed on the same layer and include substantially the same metal material. The gate electrodes 152 and 155 and the first capacitor plate 158 may include at least one of molybdenum (Mo), chromium (Cr), and tungsten (W).

An interlayer insulating layer 160 configured to cover the gate electrodes 152 and 155 is disposed on the gate insulating layer 140. The interlayer insulating layer 160 may include silicon nitride (SiNx), silicon oxide (SiOx) or tetraethoxysilane (TEOS) similar to the gate insulating layer 140; however, embodiments are not limited thereto.

A data wire including source electrodes 173 and 176 and drain electrodes 174 and 177 is disposed on the interlayer insulating layer 160. The data wire includes a data line 171, a first driving power line VDL, a second capacitor plate 178, and other lines. Further, the source electrodes 173 and 176 and the drain electrodes 174 and 177 are respectively connected to the source and the drain regions 136 and 137 of the semiconductor layers 131 and 132 through a contact opening formed on the gate insulating layer 140 and the interlayer insulating layer 160.

Accordingly, the switching thin film transistor Tr_S includes the switching semiconductor layer 131, the switching gate electrode 152, the switching source electrode 173, and the switching drain electrode 174. The driving thin film transistor Tr_D includes the driving semiconductor layer 132, the driving gate electrode 155, the driving source electrode 176, and the driving drain electrode 177. Configurations of the thin film transistors Tr_D and Tr_S are not limited to the above embodiments, and thus may be modified to have various structures that are known to and can be easily conceived by those skilled in the pertinent art.

The capacitor Cst includes the first capacitor plate 158 and the second capacitor plate 178 with the interlayer insulating layer 160 interposed therebetween.

The switching thin film transistor Tr_S may function as a switching element configured to select pixels to perform light emission. The switching gate electrode 152 is connected to the gate line 151. The switching source electrode 173 is connected to the data line 171. The switching drain electrode 174 is spaced apart from the switching source electrode 173 and connected to the first capacitor plate 158.

The driving thin film transistor Tr_D applies a driving power to the pixel electrode 211, which allows a light emitting layer 212 of a display element LED in the selected pixel to emit light. The driving gate electrode 155 is connected to the first capacitor plate 158. The driving source electrode 176 and the second capacitor plate 178 are respectively connected to the first driving power line VDL. The driving drain electrode 177 is connected to the pixel electrode 211 of the display element LED through a contact hole.

With the above described structure, the switching TFT Tr_S may be operated by a gate voltage applied to the gate line 151 and may play a role in transmitting a data voltage applied to the data line 171 to the driving TFT Tr_D. Voltage equivalent to a difference between a common voltage applied from the first driving power line VDL to the driving TFT Tr_D and the data voltage transmitted from the switching TFT Tr_S is stored in the capacitor Cst, and current corresponding to the voltage stored in the capacitor Cst flows to the light emitting element through the driving TFT Tr_D, such that the light emitting element can emit light.

A planarization layer 165 is disposed on the interlayer insulating layer 160 so as to cover the data wire patterned on the same layer including the data line 171, the first driving power line VDL, the source electrodes 173 and 176, the drain electrodes 174 and 177, the second capacitor plate 178, and the like.

The planarization layer 165 is configured to planarize a surface by eliminating or reducing steps so as to increase luminance efficiency of the light emitting element that will be formed thereon. The planarization layer 165 may include at least one of followings: polyacrylate resins, epoxy resins, phenolic resins, polyamide resins, polyimide resin, unsaturated polyester resin, polyphenylen ether resin, polyphenylene sulfide resin, and benzocyclobutene (BCB).

The pixel electrode 211 of the light emitting element is disposed on the planarization layer 165. The pixel electrode 211 is connected to the drain electrode 177 through the contact hole formed on the planarization layer 165.

At least a part of the pixel electrode 211 is disposed on the pixel region. That is, the pixel electrode 211 is disposed to correspond to the pixel region defined by the pixel defining layer 190. The pixel defining layer 190 may include resins, such as polyacrylate resins or polyimide resins.

A light emitting layer 212 is disposed on the pixel electrode 211 in the pixel region and a common electrode 213 is disposed on the pixel defining layer 190 and the light emitting layer 212. The light emitting layer 212 includes low-molecular-weight organic materials or high-molecular-weight organic materials. At least one of a hole injection layer HIL and a hole transporting layer HTL may be further disposed between the pixel electrode 211 and the light emitting layer 212. Further, at least one of an electron transporting layer ETL and an electron injection layer EIL may be further disposed between the light emitting layer 212 and the common electrode 213.

The pixel electrode 211 and the common electrode 213 may each be formed as one of the followings: a transmissive electrode, a transflective electrode, and a reflective electrode.

Transparent conductive oxide (TCO) may be used to form a transmissive electrode. The transparent conductive oxide (TCO) may include at least one of indium tin oxide (ITO), indium zinc oxide (IZO), antimony tin oxide (ATO), aluminum zinc oxide (AZO), zinc oxide (ZnO), and alloys thereof.

Metal, such as magnesium (Mg), silver (Ag), gold (Au), calcium (Ca), lithium (Li), chromium (Cr), aluminum (Al), and copper (Cu), or metal alloys thereof may be used to form a transflective and a reflective electrode. In this case, whether an electrode is a transflective type or a reflective type depends on a thickness of the electrode. Generally, the transflective electrode has a thickness of about 200 nm or less and the reflective electrode has a thickness of about 300 nm or more. As the thickness of the transflective electrode decreases, light transmittance and resistance become higher. On the contrary, as the thickness of the transflective electrode increases, the light transmittance decreases.

Further, the transflective and the reflective electrodes may have a multilayer structure including a metal layer including metal or metal alloys and a TCO layer laminated on the metal layer.

The light emitting element display device according to an embodiment may have a dual-side light emitting structure where light is emitted toward the pixel electrode 211 and the common electrode 213. In this case, both of the pixel electrode 211 and the common electrode 213 may be formed in a transmissive type or a transflective type.

The sealing member 250 may be disposed on the common electrode 213. A transparent insulating substrate including glasses or transparent materials, such as plastics, may be used as the sealing member 250. Further, the sealing member 250 may have a thin film encapsulation structure in which one or more inorganic layers and one or more organic layers are alternately laminated.

Polymer materials having transparent properties may be used to form the water-resistant coating layers 261a and 261b. For example, polyester and parylene may be used to form the water-resistant coating layers 261a and 261b. The water-resistant layers 261a and 261b may be coated by a thermal diffusion deposition method at room temperature or bonded in a film form. Further, water-resistant coating materials generally used by those skilled in the pertinent art may be applied to an embodiment.

The heat-resistant coating layers 262a and 262b have transparent properties and materials having high thermal conductivity may be used to form the heat-resistant coating layers 262a and 262b. For example, a graphite sheet, an acryl sheet, and the like may be used to form the heat-resistant coating layers 262a and 262b. Further, heat-resistant coating materials generally used by those skilled in the pertinent art may be applied to an embodiment.

Figure 5:
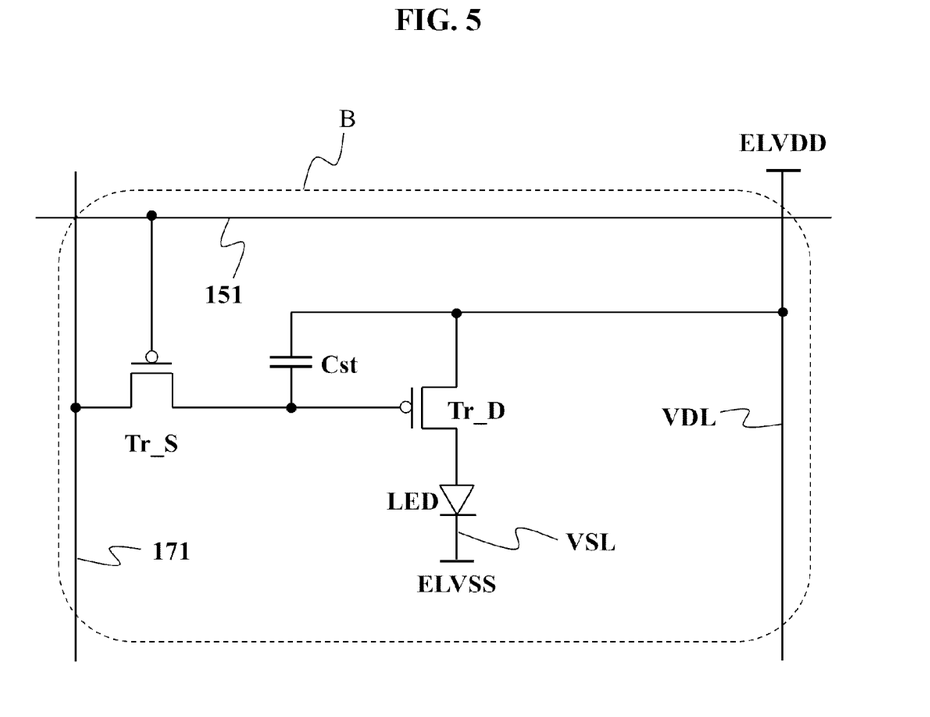
FIG. 5 is a circuit diagram illustrating an equivalent circuit of a pixel included in area B of FIG. 3.

One pixel may have a circuit configuration illustrated in FIG. 5.

FIG. 5 is a circuit diagram illustrating an equivalent circuit of a pixel included in area B of FIG. 3.

The pixel includes, as illustrated in FIG. 5, the driving TFT Tr_D, the switching TFT Tr_S, the capacitor Cst, and the light emitting element LED.

The driving TFT Tr_D is controlled by signals applied to a gate electrode thereof and is connected between the first driving power line VDL supplying the first driving voltage ELVDD and an anode electrode of the light emitting element LED. The driving switching element Tr_D adjusts an amount (a density) of a driving current flowing from the first driving power line VDL to the second driving power line VSL according to a signal magnitude applied to the gate electrode thereof.

The data switching element Tr_S is controlled by the gate signal supplied from the gate line GLn and connected to the data line DLm and the gate electrode of the driving TFT Tr_D.

The capacitor Cst is connected between the gate electrode and the anode electrode of the driving TFT Tr_D and stores a signal applied to the gate electrode of the driving TFT Tr_D.

The light emitting element LED emits light according to the driving current supplied through the driving TFT Tr_D, and thus light has different luminance values according to a magnitude of the driving current. An anode electrode of the light emitting element LED is connected to a drain electrode (or a source electrode) of the driving TFT Tr_D and a cathode electrode of the light emitting element LED is connected to the second driving power line VSL.

Returning to FIG. 1, a system SYS outputs a vertical synchronizing signal, a horizontal synchronizing signal, a clock signal, and image data through a low voltage differential signaling (LVDS) receiver and an interface circuit provided in an inside graphic controller (not shown). The vertical/horizontal synchronizing signals and the clock signal outputted from the system SYS are supplied to the timing controller TC. Further, the image data sequentially outputted from the system SYS is supplied to the timing controller TC.

The timing controller TC generates a data control signal DCS and a gate control signal GCS based on the vertical/horizontal synchronizing signals and the clock signal supplied thereto. Then, the timing controller TC supplies the data control signal DCS to the data driver DD and the gate control signal GCS to the gate driver GD.

The data driver DD performs a sampling of the image data according to the data control signal DCS supplied from the timing controller TC, performs a latching of the sampled image data corresponding to one horizontal line every horizontal period, and supplies the latched image data to the data lines DL1 to DLj. That is, the data driver DD converts the image data supplied from the timing controller TC into an analog signal (a data voltage) using a gamma voltage GMA supplied from the power supplying unit PS and supplies the signal to the data lines DL1 to DLj. The data driver DD may be installed in a non-display area of the display panel DSP.

The gate driver GD sequentially outputs the first to the $i^{th}$ gate signals according to a gate control signal GCS supplied from the timing controller TC. The $n^{th}$ horizontal line pixels are controlled by the $n^{th}$ gate signal. The $n^{th}$ gate signal is a pulse signal that keeps an active state during the $n^{th}$ horizontal period of every frame and keeps a non-active state during the other periods. I gate signals are all pulse signals that have the same pulse form but are outputted at different time points. The active state of a signal, such as the gate signal, refers to a state where a switching element receiving the signal can be turned on. Further, the non-active state of a signal, such as the gate signal, refers to a state where a switching element receiving the signal can be turned off. The first to the $i^{th}$ gate signals may have voltage of 20 [V] in an active state and −5 [V] in a non-active state. The gate driver GD may be installed in the non-display area of the display panel DSP.

The power supplying unit PS generates various power signals including the gamma voltage GMA, the first driving voltage ELVDD, and the second driving voltage ELVSS. For this purpose, although not illustrated, the power supplying unit PS includes a gamma generating circuit generating the gamma voltage GMA, a first driving power circuit generating the first driving voltage ELVDD, and a second driving power circuit generating the second driving voltage ELVSS.

Hereinafter, configurations of the retarder plate RTD and the selective polarizer S-POL will be described in more detail with reference to FIGS. 1, 6, and 7.

Figure 6:
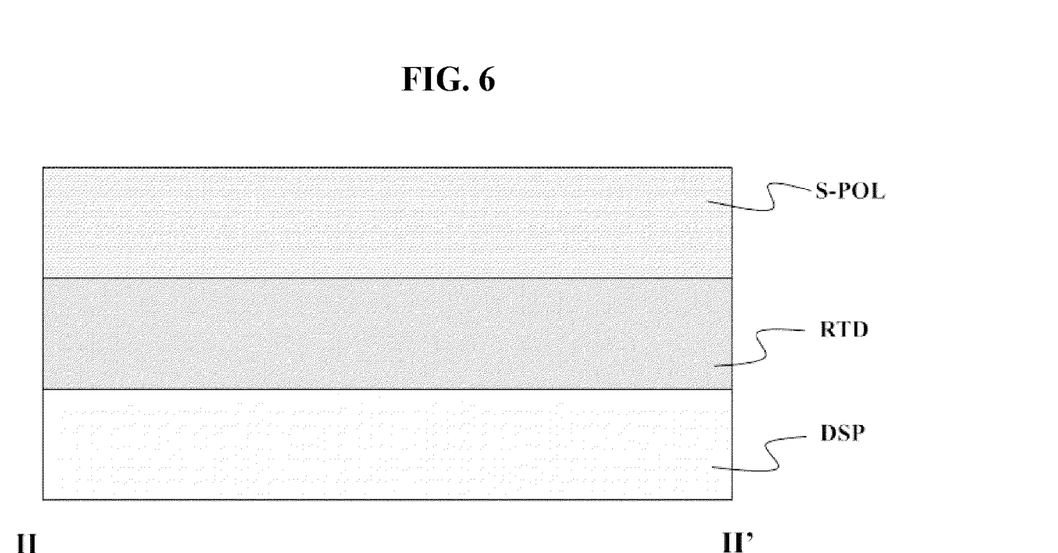
FIG. 6 is a cross-sectional view taken along a line II-II" of FIG. 1.
Figure 7:
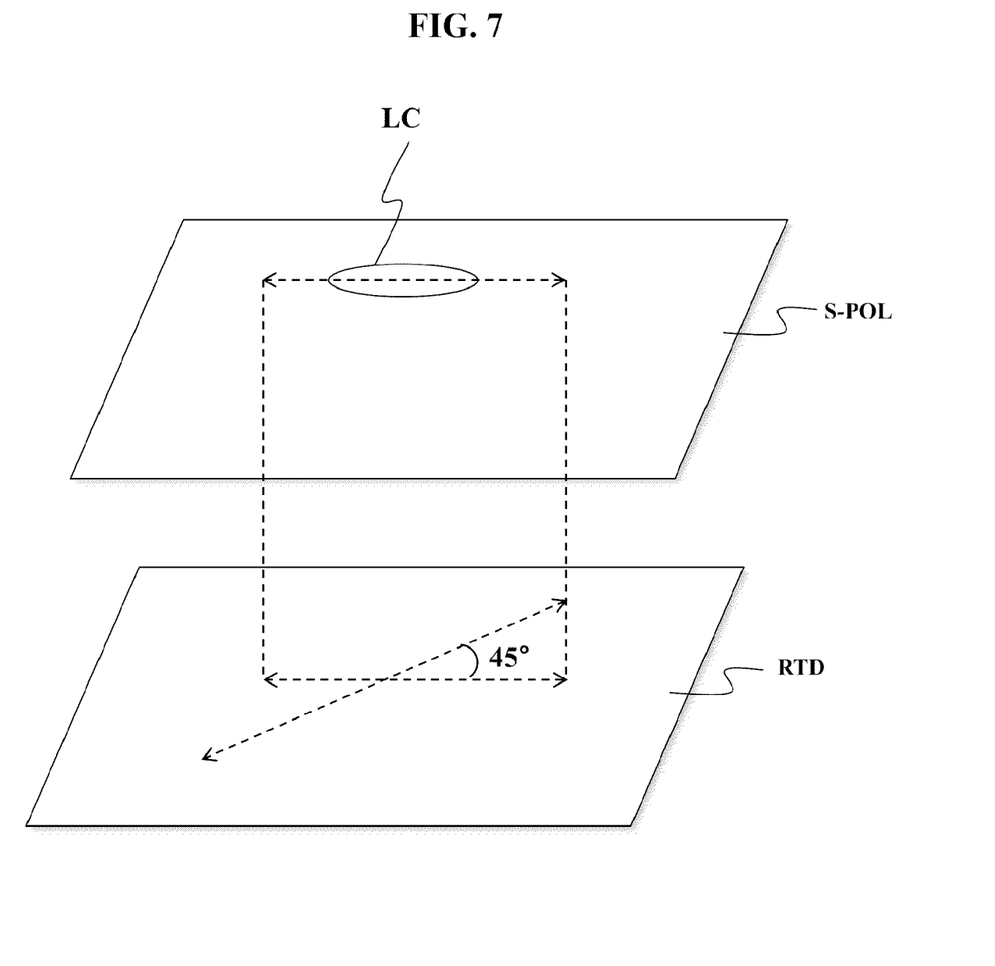
FIG. 7 is a conceptual view illustrating an angle between a major axis of liquid crystal molecules included in a selective polarizer and an optical axis of a retarder plate.

FIG. 6 is a cross-sectional view taken along a line II-II" of FIG. 1 and FIG. 7 is a conceptual view illustrating an angle between a major axis of liquid crystal molecules included in a selective polarizer and an optical axis of a retarder plate.

As illustrated in FIGS. 1 and 6, the retarder plate RTD is disposed between the display panel DSP and the selective polarizer S-POL. That is, the retarder plate is disposed on the display area of the display panel DSP and the selective polarizer S_POL is disposed on the retarder plate.

The retarder plate RTD converts light emitted from the light emitting element LED of the display panel DSP into circularly polarized light. The retarder plate RTD includes a quarter-wave plate as a principal plane. The light emitted from the light emitting element LED is incident on the principal plane of the retarder plate RTD at an angle of about 45 degrees. In a case where this light passes through the retarder plate RTD, the light is converted to circularly polarized light. The light leaving the retarder plate RTD (the circularly polarized light) is incident on the selective polarizer S-POL. The optical axis of the retarder plate forms a predetermined angle with a major axis of liquid crystal molecules LC included in the selective polarizer S-POL. For example, as illustrated in FIG. 7, in a state where the liquid crystal molecules LC are rotated to have the major axis thereof point a horizontal direction, the major axis of the liquid crystal molecule LC and the optical axis of the retarder plate RTD form an angle of about 45 degrees.

The selective polarizer S-POL converts the circularly polarized light supplied through the retarder plate RTD into linearly polarized light or allows penetration of the circularly polarized light without a polarization process. In more detail, the selective polarizer S-POL either produces linearly polarized light or allows penetration of the circularly polarized, selectively, according to an external control signal. For example, in a case where the light emitting element display device according to an embodiment receives an order to operate in a display mode, the selective polarizer S-POL converts light into linearly polarized light in response to the signal. However, in a case where the light emitting element display device according to an embodiment receives an order to operate in a light therapy mode, the selective polarizer S-POL allows light to pass through in response to the signal.

Depending on the performance of the selective polarizer S-POL, the light transmittance of the selective polarizer S-POL becomes different. For example, in a case where the selective polarizer S-POL converts light into linearly polarized light, an amount of light leaving the selective polarizer S-POL is reduced by 50% compared to an amount of light before passing through the selective polarizer S-POL. However, in a case where the selective polarizer S-POL allows light to pass through, an amount of light leaving the selective polarizer S-POL is reduced by 20% compared to the amount of light before passing through the selective polarizer S-POL. Accordingly, an amount of light suitable for the treatment may be radiated on a user in the light therapy mode. A configuration of the selective polarizer S-POL will be described in more detail below.

Returning to FIG. 1, the polarization controller PCT controls a performance of the selective polarizer S-POL. That is, the selective polarizer S-POL may either perform a linear polarization or allow penetration of light. In more detail, in a case where the light emitting element display device according to an embodiment receives an order to operate in a display mode, the polarization controller PCT generates a first control signal and transmits the first control signal to the selective polarizer S-POL. Subsequently, the selective polarizer S-POL converts light into linearly polarized light according to the first control signal. However, in a case where the light emitting element display device according to an embodiment receives an order to operate in a light therapy mode, the polarization controller PCT generates a second control signal and transmits the second control signal to the selective polarizer S-POL. Subsequently, the selective polarizer S-POL allows light to pass through according to the second control signal.

In some embodiments, the polarization controller PCT may limit the penetration in order to limit an amount of light radiation in a light therapy mode. For this purpose, the light emitting element display device according to an embodiment may further include a counter (not illustrated).

The counter is configured to count time from the time when the selective polarizer S-POL starts the light penetration and supply the counted number information to the polarization controller PCT. Subsequently, the polarization controller PCT compares the counted number supplied from the counter with a predetermined reference value and controls the operation of the selective polarizer S-POL based on the comparison result. For example, in a case where the counted number is the same as or larger than the predetermined reference value, the polarization controller PCT forcibly stops the penetration process of the selective polarizer S-POL. Further, when the light penetration is stopped, the polarization controller PCT may control the selective polarizer S-POL to further carry out a polarization process. In some embodiments, in a case where the counted number is the same as or larger than the predetermined reference value, the polarization controller PCT may control the selective polarizer S-POL to immediately start the light penetration. For example, in a case where the counted number is larger than the predetermined reference value, the polarization controller PCT may forcibly generate the first control signal and supply the first control signal to the selective polarizer S-POL.

Further, in a case where the polarization controller PCT forcibly stops the penetration process or where the counted number is larger than the predetermined reference value, the polarization controller PCT may further generate an alert.

The predetermined reference value refers to a time corresponding to the recommended daily light allowance and can be defined as follows:

$$A\ reference\ value = \{a\ recommended\ daily\ light\ allowance\ [h*uW/cm2]\}/\{a\ maximum\ output\ of\ a\ light\ therapy\ device\ [uW2/cm2]\}, \quad <FORMULA>$$

wherein the maximum output of a light therapy device refers to a maximum output of the light emitting element display device according to an embodiment.

The polarization controller PCT may be installed inside the timing controller TC of FIG. 1. Further, such a function of the polarization controller PCT may be performed by a timing controller TC instead of the polarization controller PCT.

Figure 8:
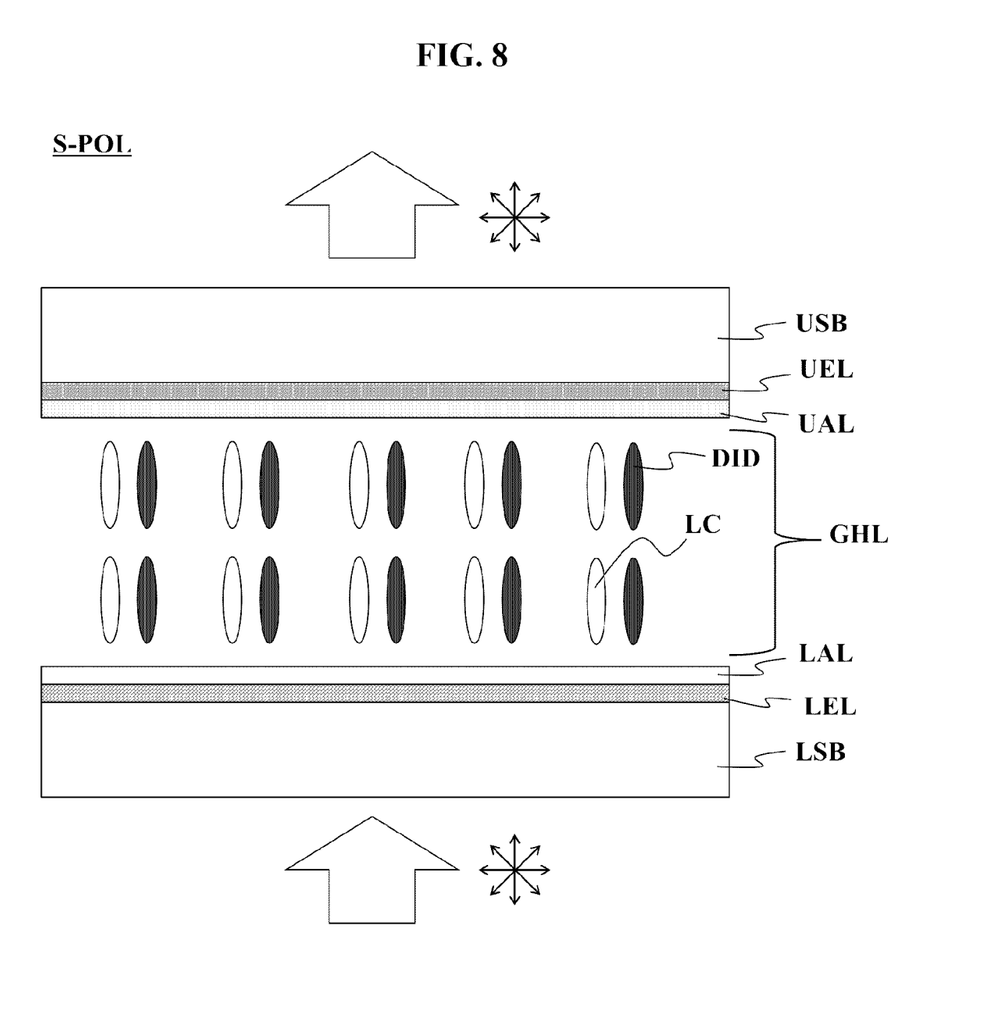
FIGS. 8 and 9 are detailed cross-sectional views illustrating the selective polarizer of FIG. 1 or 6.
Figure 9:
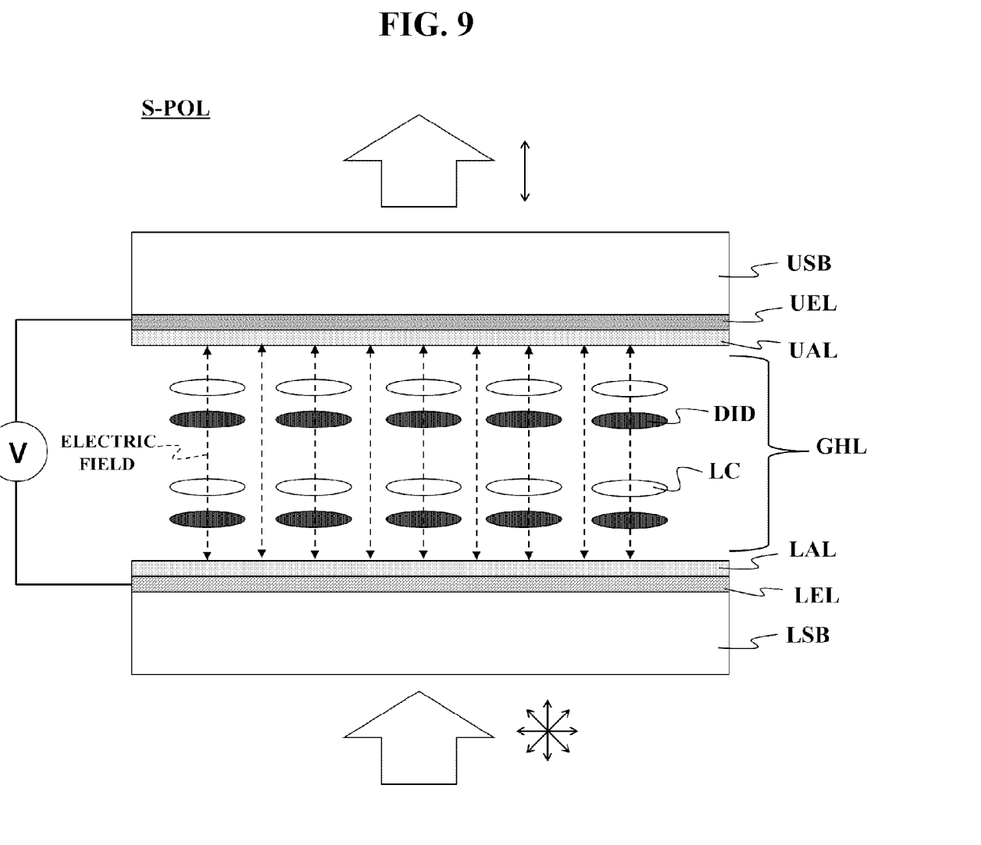

FIGS. 8 and 9 are detailed cross-sectional views illustrating the selective polarizer S-POL of FIGS. 1 and 6. More particularly, FIG. 8 illustrates an arrangement of liquid crystal molecules LC and dichroic dyes that are in a state where an electric field does not exist, and FIG. 9 illustrates an arrangement of liquid crystal molecules LC and dichroic dyes that are in a state where an electric field exists.

According to an embodiment, the selective polarizer S-POL may include, as illustrated in FIG. 8, a lower substrate body LSB, an upper substrate body USB, a guest-host layer GHL, a lower electrode LEL, an upper electrode UEL, and a lower and an upper alignment layers LAL and UAL. A guest-host polarizer may be used as the selective polarizer according to an embodiment.

A guest-host layer GHL is formed between the upper substrate body USB and the lower substrate body LSB. The guest-host layer GHL includes liquid crystal molecules LC and dichroic dyes DID. As illustrated in FIG. 8, an alignment of the liquid crystal molecules LC and the dichroic dyes DID in a state where an electric field does not exist, that is, an initial alignment direction may be vertical. In other words, a major axis of the liquid crystal molecules LC and the dichroic dyes DID may be aligned in a vertical direction. However, the liquid crystal molecules LC and the dichroic dyes DID may be initially disposed in a horizontal direction in other embodiments.

The lower electrode LEL is disposed on the lower substrate body LSB and the upper electrode UEL is disposed on the upper substrate body USB. The lower and upper electrodes LEL and UEL receive the first and the second control signals outputted from the polarization controller PCT. For example, the first control signal may include a lower voltage and an upper voltage that have a voltage difference and the lower voltage is applied to the lower electrode LEL while the upper voltage is applied to the upper electrode UEL. In some embodiments, the second control signal may include two identical voltages that do not have a voltage difference. In some embodiments, the second control signal may include one voltage applied to both of the lower and upper electrodes LEL and UEL together. The above-described voltage may be, for example, voltage of 0 [V] that is the same as ground.

The lower alignment layer LAL and the upper alignment layer UAL are configured to determine an initial alignment direction of the liquid crystal molecules LC and the dichroic dyes DID and also determine an alignment direction of the liquid crystal molecules LC and the dichroic dyes DID when the electric field is formed in the guest-host layer GHL.

As illustrated in FIG. 8, in a case where voltage of 0 [V] is applied to the grounds of the lower and upper electrodes LEL and UEL, an electric field is not formed between the lower and upper electrodes LEL and UEL. Therefore, the major axis of the liquid crystal molecules LC and the dichroic dyes DID are aligned in a vertical direction. In a case where the liquid crystal molecules LC and the dichroic dyes DID are aligned as illustrated in FIG. 8, light (circularly polarized light) supplied from the retarder plate RTD passes through the guest-host layer GHL. In other words, in a case like FIG. 8, the selective polarizer S-POL allows penetration of light.

As illustrated in FIG. 9, in a case where a lower voltage and an upper voltage that have a voltage difference are respectively applied to the lower electrode LEL and the upper electrode UEL, an electric field is formed between the lower electrode LEL and the upper electrode UEL, such that the liquid crystal molecules LC and the dichroic dyes DID are subject to the effect of the electric field, and rotate. That is, as illustrated in FIG. 9, the major axis of the liquid crystal molecules LC and the dichroic dyes DID are aligned in a vertical direction with respect to a direction of the electric field. In a case where the liquid crystal molecules LC and the dichroic dyes DID are aligned as illustrated in FIG. 9, light (circularly polarized light) supplied from the retarder plate RTD becomes linearly polarized when passing through the guest-host layer GHL. In other words, in a case like FIG. 9, the selective polarizer S-POL converts light into linearly polarized light.

Figure 10:
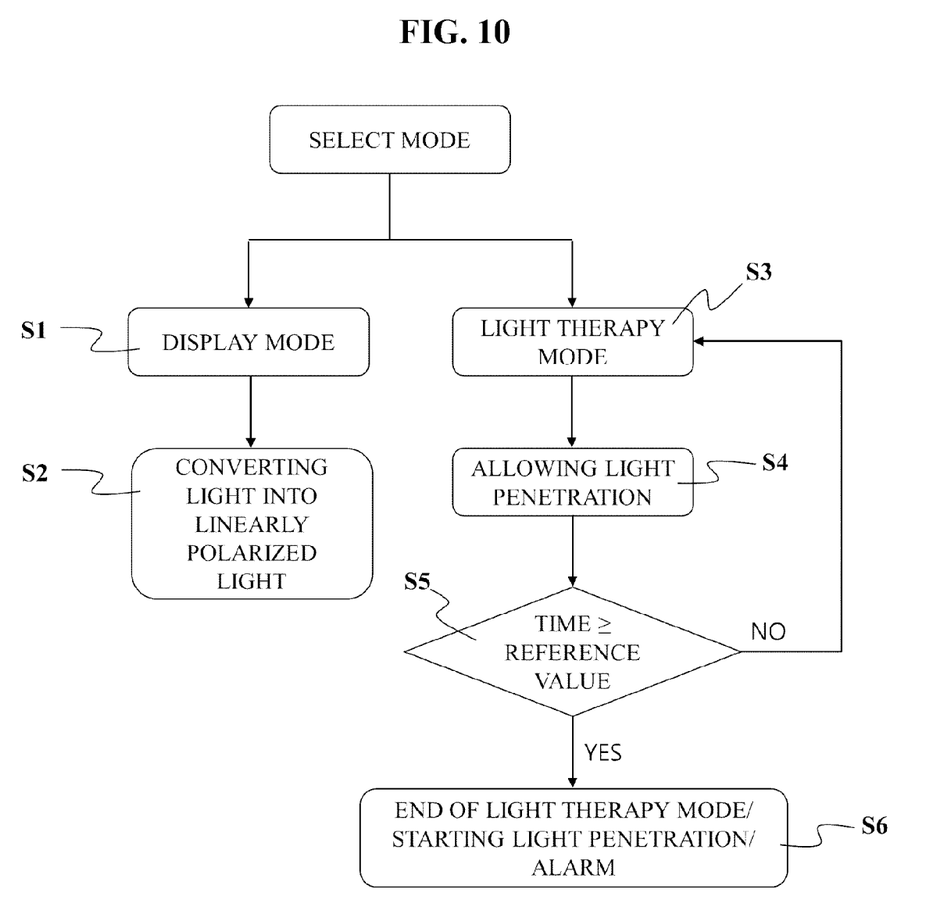
FIG. 10 is a block diagram for illustrating a method of driving the light emitting element display device having a light therapy function according to an embodiment.

FIG. 10 is a block diagram for illustrating a method of driving the light emitting element display device having a light therapy function according to an embodiment.

As illustrated in S1 and S2, in a case where a display mode is selected, the selective polarizer S-POL converts light into linearly polarized light. Accordingly, the light emitting element display device having a light therapy function functions as a display device.

However, as illustrated in S3 and S4, in a case where a light therapy mode is selected (S3), the selective polarizer S-POL allows light penetration (S4). Accordingly, the light emitting element display device having a light therapy function functions as a light therapy device.

As illustrated in S5, the operation time during which the light emitting element display device operates as a light therapy device is compared with the predetermined reference value. Thus, if the time is smaller than the predetermined reference value, the light therapy mode of S3 is maintained.

However, if the time compared in S5 is the same as or larger than the predetermined reference value, the light therapy mode is stopped and the selective polarizer S-POL converts light into linearly polarized light. Then, an alert is generated to alert users that the light therapy mode has been stopped.

The light emitting element display device having a light therapy function according to an embodiment may be used in a wide range of applications including, for example, a mobile phone, a computer monitor, a car navigation system, a television, and the like.

From the foregoing, it will be appreciated that various embodiments in accordance with the present disclosure have been described herein for purposes of illustration, and that various modifications may be made without departing from the scope and spirit of the present teachings. Accordingly, the various embodiments disclosed herein are not intended to be limiting of the true scope and spirit of the present teachings.

What is claimed is:

1. A light emitting element display device having a display function and a light therapy function, the display device comprising:
    a display panel comprising a plurality of light emitting elements;
    a retarder plate configured to convert light emitted from the plurality of light emitting elements of the display panel into circularly polarized light; and
    a selective polarizer configured to selectively convert light supplied from the retarder plate into linearly polarized light or allow penetration of the light supplied from the retarder plate,
    wherein the light emitting element display device is configured to operate in the display function when linearly polarized light is supplied from the selective polarizer, and in the light therapy function when the selective polarizer allows penetration of the light supplied from the retarder plate.

2. The light emitting element display device of claim 1, further comprising:
    a polarization controller configured to control the selective polarizer based on selection of a display mode or a therapy mode.

3. A light emitting element display device having a light therapy function, comprising:
    a display panel comprising a plurality of light emitting elements;
    a retarder plate configured to convert light emitted from the plurality of light emitting elements into circularly polarized light;
    a selective polarizer configured to selectively convert light supplied from the retarder plate into linearly polarized light or allow penetration of the light;
    a counter configured to count time from the time when the selective polarizer starts light penetration; and
    a polarization controller configured to compare the counted time supplied from the counter with a predetermined reference value and to control an operation of the selective polarizer based on a result of the comparison.

4. The light emitting element display device of claim 3, wherein the selective polarizer stops the light penetration by control of the polarization controller, when the counted time is the same as or larger than the predetermined reference value.

5. The light emitting element display device of claim 4, wherein the selective polarizer further carries out a polarization process by control of the polarization controller, when the light penetration is stopped.

6. The light emitting element display device of claim 4, wherein the polarization controller generates an alert, when the light penetration is stopped.

7. The light emitting element display device of claim 1, wherein the selective polarizer comprises:
    a lower substrate;
    an upper substrate disposed to face the lower substrate;
    a guest-host layer disposed between the lower substrate and the upper substrate;
    a lower electrode and an upper electrode respectively formed on facing surfaces of the lower substrate and the upper substrate;
    a lower alignment layer disposed on the lower electrode; and
    an upper alignment layer disposed on the upper electrode.

8. The light emitting element display device of claim 7, wherein the guest-host layer comprises liquid crystal molecules and dichroic dyes.

9. The light emitting element display device of claim 8, wherein an initial alignment direction of the liquid crystal molecules and the dichroic dyes is one of a vertical direction and a horizontal direction.

10. The light emitting element display device of claim 9, wherein a major axis of the liquid crystal molecules aligned in the horizontal direction and an optical axis of the retarder plate form an angle of about 45 degrees.

11. The light emitting element display device of claim 1, wherein the display panel comprises a substrate, and a driving circuit disposed on the substrate and configured to drive the plurality of light emitting elements; and wherein the plurality of light emitting elements is disposed on the driving circuit.

12. A method of driving a light emitting element display device having a display function and a light therapy function, the method comprising:

arranging a display panel comprising a plurality of light emitting elements, a retarder plate configured to convert light emitted from the plurality of light emitting elements of the display panel into circularly polarized light, and a selective polarizer configured to selectively convert light supplied from the retarder plate into linearly polarized light or to allow penetration of the light supplied from the retarder plate; and controlling the selective polarizer to control operation of the light emitting element display device in a display mode or in a light therapy mode wherein the light emitting element display device is configured to operate in the display function when linearly polarized light is supplied from the selective polarizer, and in the light therapy function when the selective polarizer allows penetration of the light supplied from the retarder plate.

13. A method of driving a light emitting element display device having a light therapy function, the method comprising:

arranging a display panel comprising a plurality of light emitting elements, a retarder plate configured to convert light emitted from the plurality of light emitting elements into circularly polarized light, and a selective polarizer configured to selectively convert light supplied from the retarder plate into linearly polarized light or to allow penetration of the light;

controlling the selective polarizer based on selection of a display mode or a light therapy mode;

counting time from the time when the selective polarizer starts a light penetration process; and comparing the counted time with a predetermined reference value and controlling an operation of the selective polarizer based on a result of the comparison.

14. The method of claim 13, the method further comprising controlling the selective polarizer to stop the light penetration, when the counted time is the same as or larger than the predetermined reference value.

15. The method of claim 14, the method further comprising controlling the selective polarizer to further carry out a polarization process, when the light penetration is stopped.

16. The method of claim 14, the method further comprising generating an alert when the light penetration is stopped.

* * * * *